United States Patent [19]

Martin et al.

[11] Patent Number: 4,908,361

[45] Date of Patent: Mar. 13, 1990

[54] TERAHYDROISOQUINO(2,1-c)(1,3)BENZODIAZEPINES

[75] Inventors: Lawrence L. Martin, Lebanon; Richard C. Allen, Flemington, both of N.J.

[73] Assignee: Hoechst-Roussel Incorporated, Somerville, N.J.

[21] Appl. No.: 344,799

[22] Filed: Apr. 28, 1989

[51] Int. Cl.$^4$ .................... C07D 453/00; A61K 31/55
[52] U.S. Cl. ...................................... 514/219; 540/555
[58] Field of Search ........................ 540/555; 514/219

[56] References Cited

U.S. PATENT DOCUMENTS

| | | | |
|---|---|---|---|
| 3,435,038 | 3/1969 | Hardtmann | 540/494 |
| 4,309,424 | 1/1982 | Martin et al. | 514/221 |
| 4,459,230 | 7/1984 | Martin et al. | 514/221 |
| 4,459,231 | 7/1984 | Martin et al. | 514/221 |

OTHER PUBLICATIONS

Geyer et al., J. Med. Chem., 25, 340–346 (1982).
Setescak et al., J. Med. Chem., 27, 401–404 (1984).
Martin et al., J. Heterocyclic Chem., 22, 1105–1107 (1985).

Primary Examiner—Robert Gerstl
Attorney, Agent, or Firm—Elliott Korsen

[57] ABSTRACT

Novel Tetrahydroisoquino[2,1-c][1,3]benzodiazepines are disclosed having the formula

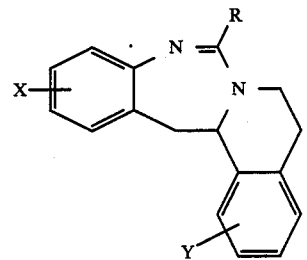

where X and Y are each independently hydrogen, halogen, loweralkyl, loweralkoxy or —CF$_3$, and R is hydrogen or loweralkyl, and the pharmaceutically acceptable acid addition salts thereof and where applicable the geometric and optical isomers and racemic mixtures thereof. The compounds of this invention display utility in enhancing memory.

11 Claims, No Drawings

TETRAHYDROISOQUINO(2,1-c)(1,3)BENZODIAZEPINES

This invention relates to tetrahydroisoquino[2,1-c][1,3]benzodiazepines of the formula

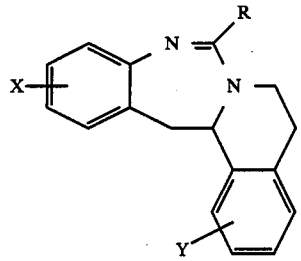

where X and Y are independently hydrogen, halogen, loweralkyl, loweralkoxy or —CF$_3$, and R is hydrogen or loweralkyl and the pharmaceutically acceptable acid addition salts thereof.

This invention also relates to novel compounds of the formula

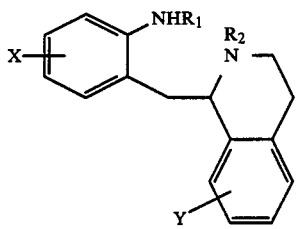

where X and Y are as defined above, R$_1$ is hydrogen and R$_3$CO, where R$_3$ is hydrogen or t-butyl, and R$_2$ is hydrogen and R$_4$CO, where R$_4$ is hydrogen and lower alkyl, which are useful as an intermediate for synthesizing compounds I.

Throughout the specification and the appended claims, a given chemical formula or name shall encompass all stereo, optical and geometrical isomers thereof where such isomers exist, as well as pharmaceutically acceptable acid addition salts thereof and solvates thereof such as for instance hydrates.

In the above definition, the term "lower" means the group it is describing contains from 1 to 6 carbon atoms. The term "alkyl" refers to a straight or branched chain hydrocarbon containing no unsaturation, e.g. methyl, ethyl, propyl, isopropyl, n-butyl, iso-butyl, tert-butyl and straight and branched-chain pentyl and hexyl, etc. The term "halogen" refers to a member of the halogen family consisting of fluorine, chlorine, bromine and iodine. The term alkoxy refers to a monovalent substituent which consists of an alkyl group linked through an ether oxygen, e.g. methoxy, ethoxy, n-propoxy, isopropoxy, n-butoxy, sec-butoxy and straight and branched chain pentoxy and hexoxy, etc.

The compounds of the present invention are prepared in the following manner. The substitutents, X, Y, R, R$_1$, R$_2$, R$_3$ and R$_4$ are as defined above unless indicated otherwise.

An N-acylated-o-toluidine of formula III is selected. These compounds are commercially available or are well known in the art and can be easily synthesized using standard conditions with known reactants. In this regard, reference is made to W. Fuhrer and H. W. Gschwend, J. Org. Chem. 44, 1133–1136 (1979) which discloses the synthesis of compounds III., where X=hydrogen.

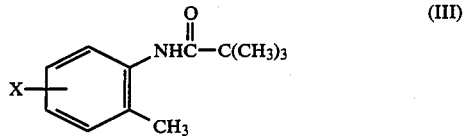

Compound III is converted to a dilithio intermediate of the formula

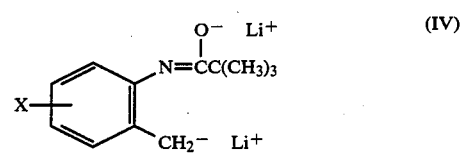

Lithiation of aromatic compounds with an n-alkyllithium compound is exemplified in J. M. Muchowski and M. Venuti, J. Org. Chem. 45, 4798–4801 (1980) and W. Fehrer and H. W. Gschwend, J. Org. Chem. 44, 1133–1136 (1979). A preferred method according to the present invention involves slowly adding a solution of an N-alkyllithium, e.g., N-butyllithium, in a solvent therefor, such as hexanes, to a solution of the N-acylated-o-toluidine (III) in an ethereal solvent such as diethyl ether, tetrahydrofuran, dimethoxyethane, and a hydrocarbon solvent, such as hexane. The ethereal solvent and hydrocarbon solvent should be substantially inert to the n-butyllithium to avoid adverse side reactions. The temperature during the addition can range from about −70° C. to about 30° C., preferably about −10° C. to about 30° C. The resulting mixture is aged from about one-half to about 5 hours, preferably about 1 to about 2 hours. The reaction is conveniently carried out at atmospheric pressure. The amount of n-butyllithium employed is up to about 10% in excess of the 2 molar equivalents required for the reaction. It is important to exclude moisture from the reaction mixture. Accordingly, the reaction is conveniently conducted in an atmosphere of a substantially dry gas, e.g., anhydrous nitrogen, etc.

Compound IV is reacted with Compound V of the formula

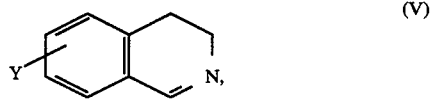

to obtain compound VI of the formula:

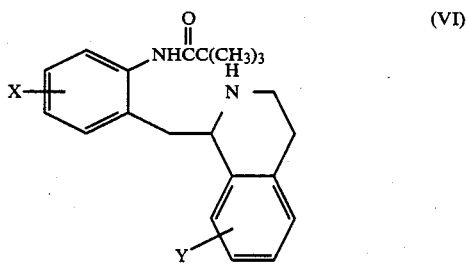

Compound V is prepared by the method of P. A. Wehrli and B. Schair, Synthesis, 4, 288 (1974). Typically, the reaction of compounds IV and V is carried out in an ethereal solvent, e.g. diethylether, tetrahydrofuran, etc., at a temperature of −20° C. to 10° C. for 1 to 5 hours to form Compound VI.

Compound VI is hydrolyzed under standard hydrolyzing conditions such as for example in an aqueous solvent, e.g. water, with a mineral acid, e.g. hydrochloric, sulfuric, etc., at a temperature of about 70° C. to reflux for 5 to 48 hours followed by standard basification with a base, e.g., sodium hydroxide, potassium hydroxide, etc. to form Compound VII (Compound II where $R_1$ and $R_2$ are hydrogen).

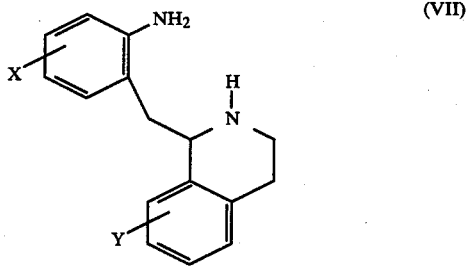
(VII)

The aromatic amine VII is reacted with the acid anhydride,

$(R_4C)_2O$ e.g., acetic anhydride under standard acylating conditions, e.g., in the presence of an organic base, e.g., pyridine, 4-dimethylaminopyridine, etc., at a temperature of −20° to 10° C. for 1 to 24 hours to form Compound VIII.

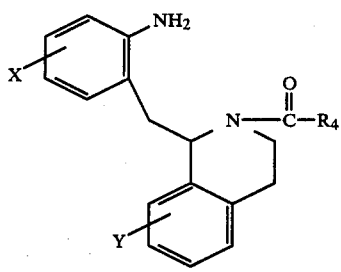
(VIII)

The aromatic acetamide is cyclized by reaction with a cyclodehydrating agent to give the compounds of formula I. Typically, Compound VIII is reacted with a cyclodehydrating agent, e.g., titanium tetrachloride, phosphorus pentachloride, phosphorus oxychloride, etc. in a suitable solvent, e.g., xylene, dichloromethane, 1,2-dichloroethane, etc. at a temperature of 0° C. to reflux for 1 to 48 hours to form Compound I of the invention.

The compounds of formula I of the present invention are useful in the treatment of various memory dysfunctions characterized by decreased cholinergic function, such as Alzheimer's disease.

This utility is demonstrated by the ability of these compounds to restore cholinergically deficient memory in the Dark Avoidance Assay, where they are in general active over a broader dose range than heretofore known compounds, a distinct therapeutic advantage.

DARK AVOIDANCE ASSAY

In this assay, mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animals' initial exposure to the test chamber, the animal re-enters the dark compartment shortly after being placed in the test chamber 24 hours later. The effect of scopolamine is blocked by an active test compound, resulting in a greater interval before re-entry into the dark compartment.

The results of an active compound are expressed as the percent of a group of animals in which the effect of scopolamine is blocked, as manifested by an increased interval between being placed in the test chamber and re-entering the dark compartment.

TABLE I

| Dark Avoidance Assay | | |
|---|---|---|
| Compound | Dose (mg/kg of body wt.) | % of Animals with Scopolamine induced memory deficit reversed |
| 8-Methyl-5,6,14,14a-tetrahydro-isoquino[2,1-c][1,3]benzodiazepine | 0.16 0.25 | 21 50 |
| Tacrine (standard) | 0.63 | 13 |
| Pilocarpine (standard) | 1.25 | 19 |

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, malic, fumaric and oxalic acids.

The active compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 75% of the weight of the unit. The amount of compound present in such composition is such that a suitable dosage will be obtained. Preferred compositions and preparations according to the present invention are prepared so that an oral dosage unit form contains between 1.0–300 mgs of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel ®, corn starch and the like; a lubricant such as magnesium strearate or Sterotex ®; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Mateials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of the aforesaid compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 mgs of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

Examples of the compounds of this invention include:
5,6,14,14-tetrahydroisoquino[2,1-c][1,3]benzodiazepine
8-methyl-5,6,14,14a-tetrahydroisoquino[2,1-c][1,3]benzodiazepine
8-ethyl-5,6,14,14a-tetrahydroisoquino[2,1-c][1,3]benzodiazepine
8-isopropyl-5,6,14,14a-tetrahydroisoquino[2,1-c][1,3]benzodiazepine
8-(n-butyl)-5,6,14,14a-tetrahydroisoquino[2,1-c][1,3]benzodiazepine
8-n-pentyl)-5,6,14,14a-tetrahydroisoquino[2,1-c][1,3]benzodiazepine
8-(n-hexyl)-5,6,14,14a-tetrahydroisoquino[2,1-c]1,3]benzodiazepine
12-chloro-5,6,14,14a-tetrahydroisoquino[2,1-c][1,3]benzodiazepine
11-chloro-8-methyl-5,6,14,14a-tetrahydroisoquino[2,1-c]1,3]benzodiazepine
12-bromo-8-ethyl-5,6,14,14a-tetrahydroisoquino[2,1-c][1,3]benzodiazepine
12-bromo-8-(n-butyl)-5,6,14,14a-tetrahydroisoquino[2,1-c][1,3]benzodiazepine
12-trifluoromethyl-5,6,14,14a-*tetrahydroisoquino*[2,1-c][1,3]benzodiazepine
10-chloro-8-methyl-5,6,14,14a-*tetrahydroisoquino*[2,1-c][1,3]benzodiazepine
10-methyl-5,6,14,14a-tetrahydroisoquino[2,1-c][1,3]benzodiazepine
12-methoxy-8-(n-propyl)-5,6,14,14a-tetrahydroisoquino[2,1-c][1,3]benzodiazepine
3-chloro-8-methyl-5,6,14,14a-tetrahydroisoquino[2,1-c][1,3]benzodiazepine
2-methoxy-8-ethyl-5,6,14,14a-*tetrahydroisoquino*[2,1-c][1,3]benzodiazepine
8-methyl-5,6,14,14a-tetrahydro-12-trifluoromethylisoquino[2,1-c][1,3]benzodiazepine
12-fluoro-5,6,14,14a-tetrahydroisoquino[2,1-c][1,3]benzodiazepine
11-fluoro-8-(n-pentyl)-5,6,14,14a-tetrahydroisoquino[2,1-c][1.3]benzodiazepine
3-chloro-12-fluoro-8-(3-methylpentyl)-5,6,14,14a-tetrahydroisoquino[2,1-c][1,3]benzodiazepine
2-fluoro-8-ethyl-5,6,14,14a-tetrahydroisoquino[2,1-c][1,3]benzodiazepine
4-chloro-8-methyl-5,6,14,14a-tetrahydroisoquino[2,1-c][1,3]benzodiazepine
13-fluoro-8-methyl-5,6,14,14a-tetrahydroisoquino[2,1-c][1,3]-benzodiazepine
3-fluoro-8-(i-butyl)-5,6,14,14a-tetrahydroisoquino[2,1-c][1,3]benzodiazepine The following examples are for illustrative purposes and are not to be construed as limiting the invention disclosed herein. The temperatures are given in degrees centigrade unless otherwise designated.

EXAMPLE 1

2,2-Dimethyl-N-[2-(1,2,3,4-tetrahydro-1-isoquinolinyl)-methylphenyl]propanamide

A stirred, chilled (−8° C.) solution of N-[(2-methyl)-phenyl]-2,2-dimethylpropanamide (3.14 g) and tetrahydrofuran (25 ml) was treated dropwise over 30 minutes with a 1.6M solution of n-butyllithium in hexanes (24 ml). The resultant solution was then stirred with cooling for one hour, during which a precipitate formed. The suspension was treated dropwise over 15 minutes with a solution of 3,4-dihydroisoquinoline (1.81 g) and tetrahydrofuran (15 ml), keeping the temperature at or below 0° C. The resultant solution was stirred with cooling for one hour and the reaction was then quenched by rapid addition of water (35 ml). This treatment produced a mixture of two immiscible liquid phases and a solid was dispersed in the upper phase. The tetrahydrofuran was removed on a rotary evaporator and the residual suspension was extracted twice with 100 ml portions of dichloromethane and dried (Na$_2$SO$_4$). The dried organic phase was filtered and evaporated to dryness to give 4.88 g of a solid. Thin layer analysis (silica gel, 5% methanol in ethyl acetate) indicated a mixture and the crude product was subjected to preparative high performance liquid chromatography (HPLC) purification (Waters Associates Prep LC/System 500A, silica gel, sample applied in CH$_2$Cl$_2$ and eluted with 5% methanol in ethyl acetate). The appropriate fractions were combined and concentrated to give 2.82 g of a solid. Recrystallization from toluene (25 ml) afforded 2.27 g (43%) of 2,2-dimethyl-N-[2-(1,2,3,4-tetrahydro-1-isoquinolinyl)methylphenyl]propanamide, m.p. 167.5°–168.5° C.

ANALYSIS: Calculated for $C_{21}H_{26}N_2O$: 78.22%C, 8.13%H, 8.69%N. Found: 78.26%C, 7.91%H, 8.62%N.

EXAMPLE 2

2-[(1,2,3,4-Tetrahydro-1-isoquinolinyl)methyl]benzenamine

A stirred solution of 2,2-dimethyl-N-[2-(1,2,3,4-tetrahydro-1-isoquinolinyl)methylphenyl]propanamide (12.5 g) and 6N hydrochloric acid solution (240 ml) was refluxed for 10½ hours and then allowed to stand overnight (about 16 hours) at room temperature. On cooling to room temperature a colorless solid separated. The mixture was decanted over crushed ice, water (300 ml) was added, and the mixture was basified with 50% sodium hydroxide solution. The turbid mixture was extracted thrice with 200 ml portions of $CH_2Cl_2$, and the combined dried ($Na_2SO_4$) organic phase was filtered and concentrated to an oil (10.15 g). On standing at 5° C. for 36 hours, a small amount of crystalline material formed. The oil was triturated with hexane and the crystalline material stirred into the oil, which resulted in complete solidification of the oil. The solid was collected by vacuum filtration, washed with hexane and dried in vacuo at room temperature to give 8.94 g (72%) of 2-[(1,2,3,4-tetrahydro-1-isoquinolinyl)methyl]benzenamine as a solid, m.p. 69°–71° C.

ANALYSIS: Calculated for $C_{16}H_{18}N_2$: 80.64%C, 7.61%H, 11.75%N. Found: 80.60%C, 7.64%H, 11.62%N.

EXAMPLE 3

2-Acetyl-1-(2-aminophenyl)methyl-1,2,3,4-tetrahydroisoquinoline

A stirred, ice water chilled solution of 2-[1,2,3,4-tetrahydro-1-isoquinolinyl)-methyl]benzenamine (4.77 g) and pyridine (40 ml) was treated dropwise over a few minutes with acetic anhydride (2.25 g). The solution was stirred for 15 min with cooling and then allowed to stand overnight (about 16 hours) at room temperature. The solution was decanted into water (250 ml), and the turbid mixture was basified with 10% sodium hydroxide solution and extracted twice with 125 ml portions of dichloromethane. The combined, dried ($Na_2SO_4$) organic phase was filtered and concentrated to give a solid. Recrystallization from toluene (30 ml) gave 3.60 g (64%) of 2-acetyl-1-(2-aminophenyl)methyl-1,2,3,4-tetrahydroisoquinoline, m.p. 142°–147.5° C.

ANALYSIS: Calculated for $C_{18}H_{20}N_2O$: 77.11%C, 7.19%H, 9.99%N. Found: 77.06%C, 7.29%H, 9.86%N.

EXAMPLE 4

8-Methyl-5,6,14,14a-tetrahydroisoquino[2,1-c][1,3]benzodiazepine

A stirred solution of 2-acetyl-1-(2-aminophenyl)-methyl-1,2,3,4-tetrahydroisoquinoline (4.21 g) and p-xylene (400 ml) was treated rapidly over one minute with a solution of titanium tetrachloride (5.83 g) and p-xylene (150 ml), which afforded a suspension. The mixture was refluxed overnight to give a dark solution with a tar-like material adhering to the flask walls and stirring shaft. The cooled mixture was decanted over crushed ice (500 ml) and the flask was thoroughly washed with water and dichloromethane to dissolve the tar. The combined mixture was basified with 10% sodium hydroxide solution to give a biphasic liquid, which contained a precipitate suspended in the aqueous phase. The phases were separated and the aqueous suspension was extracted with dichloromethane. The combined organic phase was filtered, dried ($Na_2SO_4$), filtered and concentrated to give an oil (4.81 g). The oil was diluted with ether (100 ml) and the resultant suspension was filtered to remove the amorphorous precipitate. Concentration of the filtrate gave an oil (3.85 g) which was purified by preparative HPLC. The appropriate function was concentrated to an oil which was dissolved in ether and the solution was filtered to remove a small amount of amorphorous precipitate. The filtrate was concentrated to an oil which began to slowly crystallize on storage in a refrigerator. Trituration of the oil-crystal mixture with ether gave 1.0 g (26%) of 8-methyl-5,6,14,14a-tetrahydroisoquino[2,1-c][benzodiazepine, m.p. 95°–105° C.

ANALYSIS: Calculated For $C_{18}H_{18}N_2$: 82.41%C, 6.91%H, 10.68%N. Found: 82.08%C, 7.20%H, 10.61%N.

We claim:

1. A compound of the formula

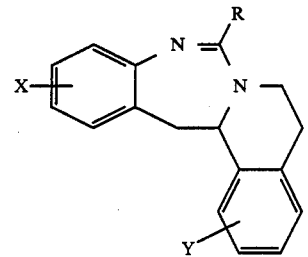

where X and Y are independently hydrogen, halogen, loweralkyl, loweralkoxy or —$CF_3$ and R is hydrogen or loweralkyl; and the pharmaceutically acceptable acid addition salts thereof and where applicable the optical isomers and racemic mixtures thereof.

2. The compound as defined in claim 1 wherein R is hydrogen, loweralkyl, and X and Y are independently hydrogen and halogen.

3. The compound as defined in claim 2 wherein X is hydrogen, Y is hydrogen and R is loweralkyl.

4. The compound as defined in claim 3 wherein R is methyl or ethyl.

5. The compound as defined in claim 4 which is 8-methyl-5,6,14,14a-tetrahydroisoquino[2,1-c][1,3]benzodiazepine.

6. The compound as defined in claim 4 which is 8-ethyl-5,6,14,14a-tetrahydroisoquino[2,1-c][1,3]benzodiazepine.

7. The compound as defined in claim 2 which is 5,6,14,14a-tetrahydroisoquino[2,1-c][1,3]benzodiazepine.

8. A memory enhancing composition which comprises an effective memory enhancing amount of a compound of the formula

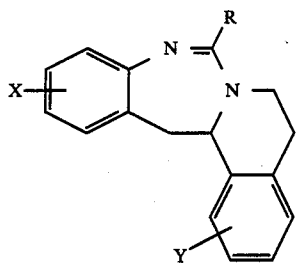

where X and Y are independently hydrogen, halogen, loweralkyl, loweralkoxy or —$CF_3$ and R is hydrogen or loweralkyl; and the pharmaceutically acceptable acid addition salts thereof and where applicable the optical isomers and racemic mixtures thereof, and a pharmaceutically acceptable carrier thereof.

9. The composition as defined in claim 8 wherein said compound is 8-methyl-5,6,14,14a-tetrahydroisoquino[2,1-c][1,3]benzodiazepine.

10. A method of enhancing the memory of an mammal in need of such enhancement which comprises administering to a mammal a memory enhancing amount of a compound having the formula

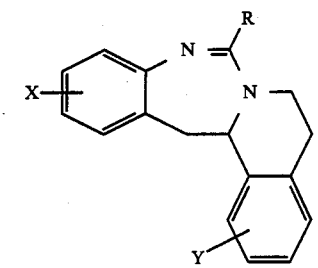

where X and Y are independently hydrogen, halogen, loweralkyl, loweralkoxy or —$CF_3$ and R is hydrogen or loweralkyl; and the pharmaceutically acceptable acid addition salts thereof and where applicable the geometric and optical isomers and racemic mixtures thereof.

11. The method as defined in claim 10 wherein said compound is 8-methyl-5,6,14,14a-tetrahydroisoquino[2,1-c][1,3]benzodiazepine.

* * * * *